United States Patent
Ambrose et al.

(10) Patent No.: US 8,986,737 B2
(45) Date of Patent: Mar. 24, 2015

(54) ANTIBIOTIC MICROSPHERES FOR TREATMENT AND PREVENTION OF OSTEOMYELITIS AND ENHANCEMENT OF BONE REGROWTH

(75) Inventors: Catherine G. Ambrose, Houston, TX (US); Terry A. Clyburn, Bellaire, TX (US); Antonio G. Mikos, Houston, TX (US)

(73) Assignees: Wm. Marsh Rice University, Houston, TX (US); Board of Regents of the Univeristy of Texas System, Austin, TX (US)

( * ) Notice: Subject to any disclaimer, the term of this patent is extended or adjusted under 35 U.S.C. 154(b) by 1011 days.

(21) Appl. No.: 12/332,026

(22) Filed: Dec. 10, 2008

(65) Prior Publication Data

US 2009/0148497 A1 Jun. 11, 2009

Related U.S. Application Data

(63) Continuation-in-part of application No. 10/655,639, filed on Sep. 5, 2003, now abandoned.

(60) Provisional application No. 60/408,496, filed on Sep. 5, 2002, provisional application No. 60/408,502, filed on Sep. 5, 2002.

(51) Int. Cl.
*A61K 9/14* (2006.01)
*A61K 9/58* (2006.01)
(Continued)

(52) U.S. Cl.
CPC .............. *A61K 9/0024* (2013.01); *A61K 9/1647* (2013.01)
USPC ........... 424/489; 424/422; 424/423; 424/501; 424/502

(58) Field of Classification Search
None
See application file for complete search history.

(56) References Cited

U.S. PATENT DOCUMENTS

| 3,236,355 A | | 2/1966 | Barnard et al. | |
| 5,385,887 A | * | 1/1995 | Yim et al. | ...................... 514/8.8 |

(Continued)

FOREIGN PATENT DOCUMENTS

| CN | 1280493 A | 1/2001 |
| CN | 1356892 A | 7/2002 |

(Continued)

OTHER PUBLICATIONS

EPO Supplemental Search Report dated Oct. 6, 2008 for Application No. EP 0375460.8 and Annex thereto; 6 pgs.
(Continued)

*Primary Examiner* — Lakshmi Channavajjala
(74) *Attorney, Agent, or Firm* — Conley Rose, P.C.

(57) ABSTRACT

A method of treating or preventing infection at a surgical site comprising a bony defect and an implanted metal device is disclosed. Biodegradable microspheres are placed at the site and are capable of near-linear controlled release of an antibiotic agent for a predetermined period of time. The microspheres are configured to be large enough to avoid being phagocytosed and removed from the body, and small enough in diameter to not physically inhibit bone growth at said bony defect site. The microspheres are formed of polylactic-co-glycolic acid (PLGA), with or without polyethylene glycol (PEG), and sufficient antibiotic agent to produce bactericidal levels in body tissues. The microspheres exhibit near-linear delivery of the antibiotic agent for at least 4 weeks at levels exceeding the minimum inhibitory concentration (MIC) for organisms commonly found to be the cause of infections, and facilitate bone ingrowth or regrowth at the site.

21 Claims, 5 Drawing Sheets

(51) Int. Cl.
A61K 9/00 (2006.01)
A61K 9/16 (2006.01)

(56) References Cited

U.S. PATENT DOCUMENTS

| | | | |
|---|---|---|---|
| 5,569,468 | A | 10/1996 | Modi |
| 5,578,650 | A | 11/1996 | Delgado et al. |
| 5,599,889 | A | 2/1997 | Stover et al. |
| 5,622,498 | A | 4/1997 | Brizzolara et al. |
| 5,662,938 | A | 9/1997 | Vert et al. |
| 5,690,954 | A | 11/1997 | Illum et al. |
| 5,718,921 | A | 2/1998 | Mathiowitz et al. |
| 5,733,567 | A | 3/1998 | Arola et al. |
| 5,766,631 | A * | 6/1998 | Arnold ........................ 424/486 |
| 5,858,531 | A | 1/1999 | Chanite et al. |
| 5,869,103 | A | 2/1999 | Yeh et al. |
| 5,922,357 | A | 7/1999 | Coombes et al. |
| 5,980,947 | A | 11/1999 | Yamakawa et al. |
| 5,993,855 | A | 11/1999 | Yoshimoto et al. |
| 6,149,944 | A | 11/2000 | Jeong et al. |
| 6,153,210 | A | 11/2000 | Roberts et al. |
| 6,197,346 | B1 | 3/2001 | Mathiowitz et al. |
| 6,207,197 | B1 | 3/2001 | Illum et al. |
| 6,214,387 | B1 | 4/2001 | Berde et al. |
| 6,217,911 | B1 | 4/2001 | Vaugn et al. |
| 6,248,345 | B1 | 6/2001 | Goldenheim et al. |
| 6,309,669 | B1 | 10/2001 | Setterstrom et al. |
| 6,410,056 | B1 | 6/2002 | Setterstrom et al. |
| 6,461,631 | B1 | 10/2002 | Dunn et al. |
| 6,555,138 | B1 | 4/2003 | Karlsson et al. |
| 6,613,810 | B1 | 9/2003 | Ejiri et al. |
| 2002/0051749 | A1 | 5/2002 | Faisant et al. |

FOREIGN PATENT DOCUMENTS

| | | |
|---|---|---|
| EP | 0709085 | 5/1996 |
| WO | 9937706 | 7/1999 |
| WO | 0074650 | 12/2000 |
| WO | 0226215 | 4/2002 |
| WO | 0245689 | 6/2002 |

OTHER PUBLICATIONS

EPO Patent Examination Report dated Sep. 15, 2009 for Application No. EP 03754460.8; 8 pgs.
Indian Patent Office First Office Action dated Nov. 14, 2006 for Application No. 1353/DELNP/2005; 6 pgs.
Indian Patent Office Second Office Action dated Oct. 1, 2007 for Application No. 1353/DELNP/2005; 5 pgs.
Summary of Examiner Interview and Allowance by Indian Patent Office with claims, dated Nov. 14, 2007; 6 pgs.
Indian Patent Office, Patent Grant dated Dec. 21, 2009; 1 pg.
Mexican Institute of the Industrial Property, First Office Action dated Jun. 2009 for Application No. PA/a/2005/002589; 1 pg. (English Summary).
Mexican Institute of the Industrial Property, Second Office Action dated Oct. 2009 for Application No. PA/a/2005/002589; 4 pgs. (English Summary).
Mexican Institute of the Industrial Property, Third Office Action dated Jun. 29, 2010 for Application No. PA/a/2005/002589; 3 pgs. (English Summary ).
Chinese Patent Office Decision on Rejection for Application No. 03824634.1 dated Jul. 10, 2009 (Translation); 10 pgs.
Chinese Patent Office Notification of Reexamination for Application No. 03824634.1 dated May 19, 2010 (Translation); 11 pgs.
Canadian Intellectual Property Office, First Office Action for Application No. 2497973 dated May 18, 2010; 6 pgs.
Australian Government IP Australia, Notice of Acceptance for Application No. 2003272284 dated Feb. 19, 2009; 3 pgs.
Ramchandani, M., et al., "In vitro and in vivo release of ciprofloxacin from PLGA 50:50 implants" Circulation, Journal of Controlled Release, vol. 54, No. 2, pp. 167-175, 1998.
Ueng, Steve S.W. et al., "In vivo study of hot compressing molded 50:50 poly (DL-lactide-co-glycolide) antibiotic beads in rabbits" Circulation, Journal of Orthopedic Research, vol. 20, No. 4, pp. 654-661, Feb. 20, 2002.
Price, J.S. et al., "Controlled release of antibiotics from coated orthopedic implants" Circulation, Journal of Biomedical Materials Research Part A, vol. 30, pp. 281-286, 1996.
Yan, Changhong et al., "Characterization and morphological analysis of protein-loaded poly (lactide-co-glycolide) microparticles prepared by water-in-oil-in-water emulsion technique" Circulation, Journal of Controlled Release, vol. 32, No. 3, pp. 231-241, 1994.
Garvin, K.L. et al., "Polylactide/polyglycolide antibiotic implants in the treatment of osteomyelitis. A canine model" Circulation, The Journal of Bone and Joint Surgery, vol. 76, No. 10, pp. 1500-1506, 1994.
Martinez, B., et al., "In vitro ciprofloxacin release from poly (Lactide-Co-Glycolide) microspheres" Circulation, Journal of Microencapsulation, Taylor and Francis, Basingstoke, GB, vol. 14, No. 2, pp. 155-161, Mar. 1, 2007.
Lin, Song-Shu et al., "Development of a biodegradable antibiotic delivery system", Circulation, Clinical Orthopaedics and Related Research, No. 362, pp. 240-250, May 1999.
King, Timothy W. et al., "Development and in vitro characterization of vascular endothelial growth factor (VEGF)-loaded poly(DL-lactic-co-glycolic acid) /poly(ethylene glycol) microspheres using a solid encapsulation/single emulsion/solvent extraction technique" Circulation, Journal of Biomedical Materials Research, vol. 51, No. 3, pp. 383-390, 2000.
U.S. Patent and Trademark Office, First Office Action for U.S. Appl. No. 10/655,639 dated Jan. 25, 2007; 8 pgs.
Response to U.S. Patent and Trademark Office, Office Action dated Jan. 25, 2007, filed Apr. 24, 2007 for U.S. Appl. No. 10/655,639; 8 pgs.
U.S. Patent and Trademark Office, Office Action dated Jul. 13, 2007 for U.S. Appl. No. 10/655,639; 8 pgs.
Response to U.S. Patent and Trademark Office, Office Action dated Jul. 13, 2007, filed Sep. 12, 2007 for U.S. Appl. No. 10/655,639; 2 pgs.
U.S. Patent and Trademark Office, Office Action dated Dec. 27, 2007 for U.S. Appl. No. 10/655,639; 4pgs.
Response to U.S. Patent and Trademark Office, Office Action dated Dec. 27, 2007, filed Mar. 27, 2008 for U.S. Appl. No. 10/655,639; 7 pgs.
U.S. Patent and Trademark Office, Final Office Action dated Jul. 10, 2008 for U.S. Appl. No. 10/655,639; 10 pgs.

* cited by examiner

ANTIBIOTIC MICROSPHERES FOR TREATMENT AND PREVENTION OF OSTEOMYELITIS AND ENHANCEMENT OF BONE REGROWTH

CROSS-REFERENCE TO RELATED APPLICATIONS

This application is a continuation-in-part of U.S. patent application Ser. No. 10/655,639, filed Sep. 5, 2003, which claims priority under 35 U.S.C. §119(e) of U.S. Provisional Application No. 60/408,496, filed Sep. 5, 2002 and U.S. Provisional Application Ser. No. 60/408,502, filed Sep. 5, 2002, the disclosures of said applications are hereby incorporated herein by reference.

BACKGROUND

1. Technical Field

This invention relates generally to microspheres capable of time releasing a drug and, more particularly to microspheres for implantation, injection, or other placement totally or partially within the body that are capable of near-linear controlled release of an antibiotic for an extended period of time, and to their methods of use for the treatment, deterrence and prevention of infections involving the body.

2. Description of the Prior Art

Historically, osteomyelitis treatment has consisted of debridement of infected tissues, irrigation with an antiseptic solution, and four to six weeks of parenteral antibiotic treatment. Due to poor penetration of the antibiotic into the infected bone site, high serum concentrations of the antibiotic need to be employed for extended periods of time in order to produce bactericidal levels within the bone tissue. These high serum levels can be associated with nephrotoxicity or ototoxicity, and can cause gastroinstestinal side effects. Due to the morbidity associated with high serum levels of antibiotics, many local delivery methods have been described including bone cement with antibiotics, collagen sponge with gentamycin, polymeric carriers with various antibiotics, and calcium sulfate carriers of antibiotics.

The need for a local drug delivery system to deliver antibiotics directly to the infection site led many physicians to mix antibiotics and polymethyl methacrylate (PMMA) bone cement into beads and place these beads into the debrided bone defect. PMMA has been used very successfully to deliver high levels of antibiotics locally without measurable systemic levels, but has several drawbacks. PMMA does not resorb and therefore a second surgery is required to remove the cement, as the cement is not biodegradable and may become a nidus for infection. Additionally, the elution of the antibiotic is nonlinear and most of the antibiotic mixed into the PMMA is permanently trapped in the cement. These drawbacks have led many researchers to develop bioresorbable delivery systems for local administration of antibiotics into infected tissue.

Infection may complicate any surgical treatment. Areas of high risk include fractures of bone treated with metal rods, plates or external fixators. The risk is particularly high if the fracture was open (compound fractures). Other surgical procedures are also at risk including vascular bypass surgery with the use of artificial graft material, general surgical procedures such as hernia repair and various procedures performed about the uterus and bladder. Once established, these infections are typically treated with surgical drainage and systemic antibiotics. Just as in the treatment of osteomyelitis, the treatment for infection may be prolonged, costly and may fail. There exists a need for a safe, effective local antibiotic delivery device that will improve healing and prevent complications.

BRIEF SUMMARY

In accordance with certain embodiments of the invention, biodegradable microspheres are implanted, injected, or otherwise placed totally or partially within the body, and are capable of near-linear controlled release of an antibiotic for a predetermined period of time for the treatment and prevention of infections involving the body. The microspheres are formed of polylactic-co-glycolic acid (PLGA) and an effective amount of antibiotic sufficient to produce bactericidal levels in body tissues, and in some embodiments include polyethylene glycol (PEG). The microspheres exhibit near-linear delivery of the antibiotic for at least 4 weeks at levels exceeding the minimum inhibitory concentration (MIC) for organisms commonly found to be the cause of infections. The microspheres allow antibiotics to be delivered at the time of various surgical treatments to decrease the occurrence of infection, and may be used for the treatment of open fractures, open reduction and internal fixation with metallic fixation of fractures, placement of joint replacement devices, and placement of various graft materials used in cardiovascular, general, gynecologic, and neurosurgical procedures.

In accordance with certain embodiments, antibiotic microspheres are provided for the treatment and prevention of infections that are capable of near-linear release of the antibiotic for an extended period of time, and at levels exceeding the minimum inhibitory concentration (MIC) for organisms commonly found to be the cause of infection.

In accordance with certain embodiments, a biodegradable microsphere antibiotic delivery system is provided for the treatment and prevention of infections and osteomyelitis that eliminates the need for an additional surgery to remove the drug carrier.

In accordance with certain embodiments of the invention antibiotic microspheres for the treatment and prevention of infections and osteomyelitis are provided that may remain at the site of implantation and do not inhibit tissue regeneration.

Certain embodiments of the invention provide antibiotic microspheres for the treatment and prevention of infections that deliver antibiotics at the time of various surgical treatments to decrease the occurrence of infection.

Certain embodiments of the invention provide antibiotic microspheres for the treatment and prevention of infections that can be easily and quickly implanted, injected, or otherwise placed totally or partially within the body at a site of actual or potential infection.

Certain embodiments of the invention provide antibiotic microspheres for the treatment, deterrence or prevention of infections that can be placed at a site of at a site of placement of metal rods, plates or metallic fixators, of joint replacement devices, and of graft materials used in cardiovascular, general, gynecologic, and neurosurgical procedures.

In accordance with certain embodiments a method is provided that comprises placing within the body biodegradable microspheres that are capable of near-linear controlled release of an antibiotic for a predetermined period of time for the treatment and prevention of infections involving the body. In various embodiments the microspheres are implanted, injected, or otherwise placed totally or partially within the body of an individual to treat or prevent an infection. The microspheres are formed of polylactic-co-glycolic acid (PLGA) and an effective amount of antibiotic sufficient to produce bactericidal levels in body tissues. In some embodiments the microspheres are formed of a mixture of PLGA and polyethylene glycol (PEG). The microspheres exhibit near-linear delivery of the antibiotic for at least 4 weeks at levels exceeding the minimum inhibitory concentration (MIC) for organisms commonly found to be the cause of infections. The microspheres allow antibiotics to be delivered at the time of various surgical treatments to decrease the occurrence of infection, and may be used for the treatment of open fractures, open reduction and internal fixation with metallic fixation of fractures, placement of joint replacement devices, and placement of various graft materials used in cardiovascular, general, gynecologic, and neurosurgical procedures.

In accordance with certain embodiments of the invention, a method of treating or preventing infection of a bony defect in the body of a patient is provided that comprises: surgically implanting a metal device into the patient at the bony defect site; and implanting a multiplicity of microspheres at the site. The microspheres contain an antibiotic agent and have a diameter large enough to avoid being phagocytosed and removed from the body, and are also small enough in diameter to not physically inhibit bone growth at the bony defect site. In some embodiments, the microspheres are formulated to gradually release the antibiotic agent at the bony defect site over at least a 4-week period. The method further includes allowing the microspheres to remain at the implant site to deter infection in the bony defect without inhibiting bone regrowth in the presence of the implanted metal device at the implant site.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

Figure 1:
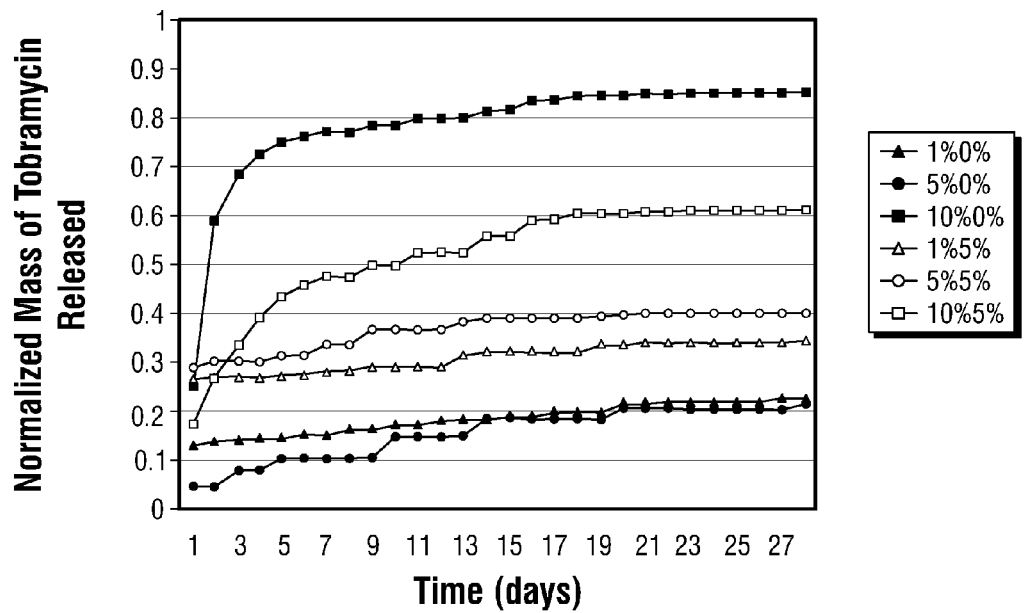
FIG. 1 is a graph illustrating the in-vitro elution of the various microsphere formulations.

The microspheres containing the antibiotic substance according to the present invention can be made of varying amounts of polylactic-co-glycolic acid (PLGA) with or without polyethylene glycol (PEG), and an effective cephalosporin antibiotic, using a water-in-oil-in-water (W/O/W), double-emulsion-solvent-extraction technique. In some embodiments, the biodegradable microspheres are formed of from about 85% to about 99% by weight of polylactic-co-glycolic acid (PLGA) in a ratio of 50% lactic to 50% glycolic acid, from about 0% to about 5% by weight of polyethylene glycol (PEG); and an effective amount of an antibiotic agent sufficient to produce bactericidal levels in body tissues. The microspheres are characterized in that they exhibit near-linear delivery of the antibiotic agent for at least 4 weeks at levels exceeding the minimum inhibitory concentration (MIC) for organisms commonly found to be the cause of infections. These and other embodiments of the present invention will be more clearly understood with reference to the following examples, which are not to be construed to limit the scope of the invention.

Example 1

PLGA/Tobramycin Drug Delivery System

Preparation of Microspheres

In the following examples the polylactic-co-glycolic acid (PLGA) used was a high molecular weight blend of 50% lactic to 50% glycolic acid (Medisorb®), from Alkermes, Cincinnati, Ohio. Polyethylene glycol (PEG) and polyvinyl alcohol (PVA) were purchased from Sigma Aldrich, of St. Louis, Mo. Tobramycin (Nebcin®), from Eli Lilly, Indianapolis, Ind. was purchased in powder form, and all remaining chemicals were purchased from Fisher Scientific (Pittsburgh, Pa.).

Microparticles were prepared in many blends of PLGA/PEG/tobramycin using an established water-in-oil-in-water (W/O/W), double-emulsion-solvent-extraction technique. The size distribution of the microparticles was measured with a Coulter counter multisizer (model 0646, Coulter Electronics, Hialeah, Fla.) after suspending the particles in an Isoton II solution (Coutler Electronics).

The entrapment efficiency of the formulation was determined in duplicate by normalizing the amount actually entrapped to the starting amount, using the established solvent-extraction technique. 10 mg of microparticles was dissolved in 1 ml of dichloromethane for 6 hours at room temperature. The tobramycin was then extracted from the organic phase to the aqueous phase by mixing 1 ml PBS and removing the aqueous portion. This was repeated every six hours for twenty-four hours and all aqueous aliquots tested for tobramycin concentration.

All tobramycin concentrations determinations were performed using fluorescence polarization immunoassay (Abbot TDx System). Sensitivity of the tobramycin assay is defined as the lowest measurable concentration which can be distinguished from zero with 95% confidence and was determined to be 0.18 microgram per milliliter.

In-Vitro Elution Rate Determination

By dry weight, the percentage of PEG in the formulations was either 0% or 5%, and the percentage of tobramycin was either 1%, 5%, or 10%. In all, six different formulations were studied for tobramycin elution rates. 25 mg amounts of microparticles were measured and placed into 2 ml glass vials containing 1 ml PBS. Each microparticle formulation was tested in triplicate and placed in a water bath at 37° C. After 24 hours, the vials were centrifuged and the supernatant removed for tobramycin assay. 1 ml of PBS was added to the vials and the vial replaced in the water bath. This was repeated once daily for one week, and then every second day for three additional weeks.

In-Vivo Drug Release Characteristics

Two formulations were studied in a mouse muscle pouch model, the 10% tobramycin with either 0% or 5% PEG. 60 adult female ICR mice, weighing 20-24 g were used for this investigation. Each animal was anesthetized using ketamine (150 mg/kg) and xylazine (6 mg/kg) IP injection. A small incision was made over the right quadriceps muscle and a small pouch was made in the muscle by blunt dissection. In thirty mice, 5 mg of microspheres containing 10% tobramycin and 0% PEG were implanted into the pouch; in the remaining thirty mice, microspheres containing 10% tobramycin and 5% PEG were implanted. Each pouch was closed with a nonabsorbable suture to mark the location. The skin was closed with resorbable suture. All animals ambulated normally throughout the study, and no signs of local inflammation (swelling, tenderness) were visible.

For each of the two microsphere formulations tested, the mice were divided into 5 groups of six mice each and sacrificed sequentially at one day, four days, seven days, twenty-two days, and either 33 or 40 days post-surgery. At sacrifice, the scarred incision was reopened and the pouch located by the suture. Approximately 0.1 g of tissue surrounding the suture was removed. Half of the tissue was placed in formalin for subsequent histological evaluation. The remaining half of the tissue was weighed and placed in 0.5 ml PBS and macerated. The tissues from three mice in each group were randomly pooled together in each vial such that there were two vials for each timepoint for each group. The tissue was incubated for 2 hours at 37° C. After incubation, the vial was centrifuged and the supernatant filtered for tobramycin analysis. Tobramycin concentration is presented as amount of tobramycin per weight of muscle tissue.

The preserved tissue was cut into 5 µm sections and stained with an H&E stain. Each slide was graded for inflammation by a blinded pathologist according to the following scale: 1 for no or minimal inflammation, 2 for moderate inflammation, and 3 for marked or severe inflammation.

In Vitro Results

The in-vitro elution of the 6 microsphere formulations is shown in FIG. 1. In this figure, the amount of drug released has been normalized to the total amount present in the implanted microspheres. The entrapment efficiency for each formulation of microsphere ranged between 40.24% to 61.8%, as shown in Table 1 below. In general, adding PEG increased the entrapment efficiency. All microspheres were found to be on average 20±1.6 µm in diameter.

Each formulation had a large initial release of tobramycin in the first 24 hours, followed by a few days of lowered release and then a few weeks of nearly steady release. Linear fits of the elution curves during the 7-28 day time period demonstrated correlations ranging from $r^2$=0.7748 to 0.9770, indicating that the release of antibiotic is very linear over this time period. Table 1 shows the calculated average linear release of tobramycin for each formulation for days 7 through 28 in absolute amounts and percentage of total amount of drug.

TABLE 1

Microsphere Characteristics and in vitro Elution

| Microsphere Formulation | | | Entrapment | Average Release | |
|---|---|---|---|---|---|
| % PLGA | % Tobramycin | % PEG | Efficiency | µg/day | %/day |
| 99 | 1 | 0 | 42.8% | 0.3852 | 0.48 |
| 95 | 5 | 0 |  | 2.3586 | 0.37 |
| 90 | 10 | 0 | 45.8% | 4.4510 | 0.41 |
| 94 | 1 | 5 | 61.8% | 0.5131 | 0.33 |
| 90 | 5 | 5 | 40.2% | 1.3415 | 0.27 |
| 85 | 10 | 5 | 52.4% | 8.7916 | 0.67 |

Figure 2:
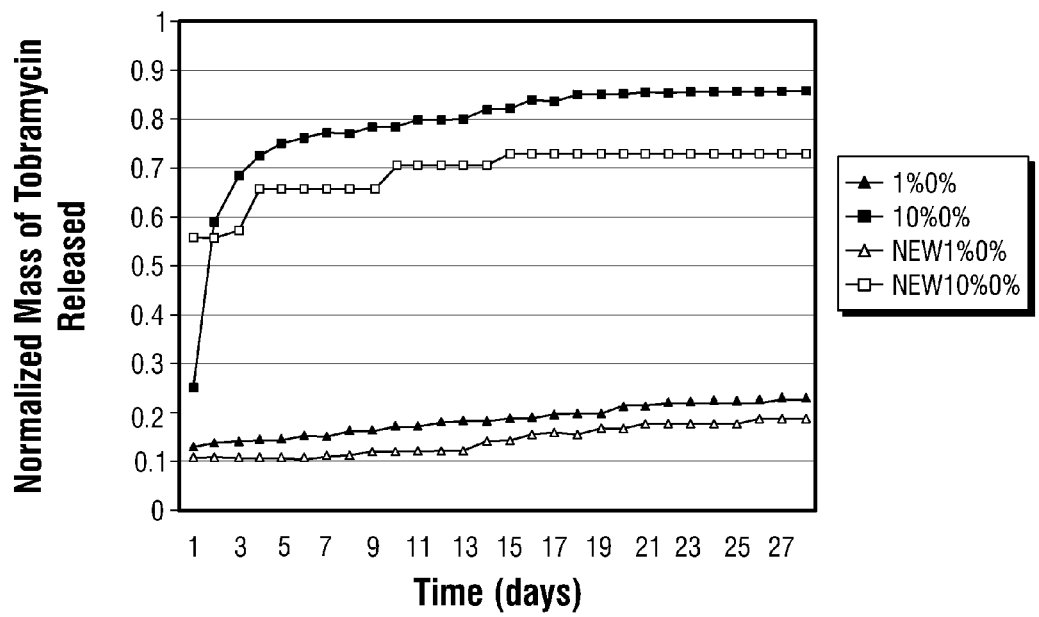
FIG. 2 is a graph illustrating the results of a repeatability study of the in vitro elution rates where two of the formulations were manufactured more than one year apart.

A repeatability study was performed in which two of the formulations were manufactured more than one year apart. The in vitro elution rates for these experiments is presented in FIG. 2.

In Vivo Results

Figure 3:
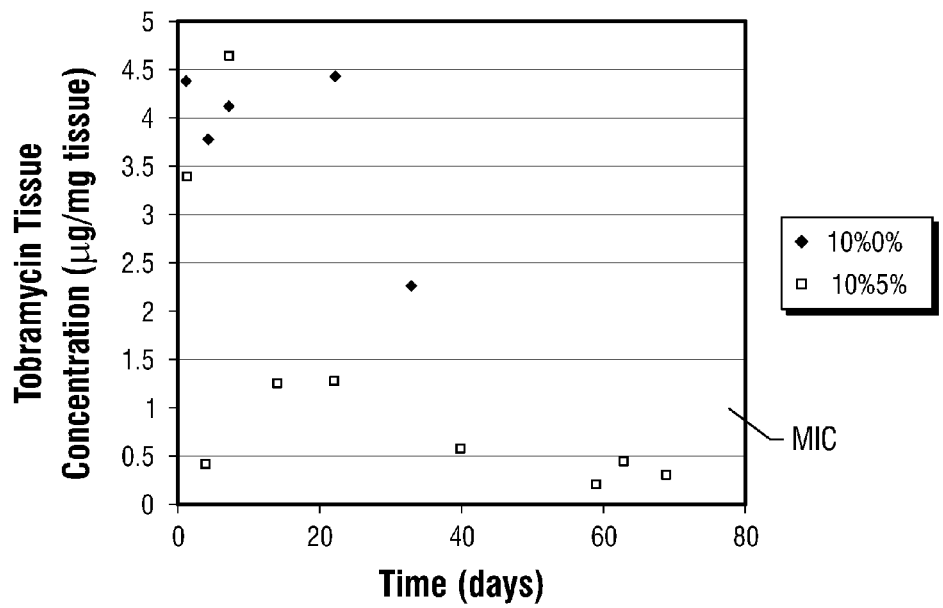
FIG. 3 is a graph illustrating the in-vivo tobramycin concentrations in tissue over time for two of the formulations tested.

The in-vivo tobramycin concentrations are shown in FIG. 3 for the two formulations tested. The MIC of tobramycin against S. aureus is shown for comparison. The histological scores for the quadriceps tissue is shown in Table 2 below.

TABLE 2

Histological Scoring for Quadriceps Tissue

| | Histological Inflammation Score | |
|---|---|---|
| Timepoint Days | 10% tobramycin 0% PEG | 10% tobramycin 5% PEG |
| 1 | 1 | |
| 4 | 3 | |
| 7 | 3 | |
| 14 | | |
| 21 | 1 | 1 |
| 30-40 | 1 | |

The results of the in-vitro studies demonstrate that both changing the antibiotic concentration and the concentration of PEG can alter the elution characteristics of the antibiotic. In general, increasing the concentration of either component decreased the rate at which the antibiotic was released, although the initial burst of drug released increased with increasing antibiotic or PEG concentration. In all formulations the release rate leveled off to a near linear rate after the first week and remained steady for the next three weeks. At these linear release rates, it was determined that the formulation with 10% tobramycin and 0% PEG would have released all of the antibiotic in 60 days. By contrast, the formulation with 1% tobramycin and 0% PEG would take nearly 186 days to release all of the antibiotic. As can be seen from FIG. 2, the different microsphere formulations can be reproducibly manufactured.

The results of the in-vivo study demonstrate that these microspheres do not elicit an extreme inflammation response. The inflammation did increase to marked by day 3, but returned to minimal levels by day 7 and remained there for the next three weeks. This inflammation was localized to the implant site and did not produce visible signs of inflammation nor did it affect the animal's appetite or ambulation.

A major result was that although the in-vitro elution characteristics demonstrated a larger linear release rate of tobramycin for the 10% tobramycin 5% PEG formulation, the in-vivo results showed higher tissue concentrations of tobramycin for the 10% tobramycin 0% PEG formulation, in fact, although the tissue levels were measurable for the 10% tobramycin 5% PEG formulation throughout the study, they remained at or below the minimum inhibitory concentration (MIC) for S. aureus in the second through fourth week. By contrast, the 10% tobramycin 0% PEG formulation resulted in tissue concentrations at least twice the MIC for the entire study period.

Microspheres were visible with the histological examination indicating that the microspheres do remain at the site of implantation for at least thirty days, and, indeed, measurable tobramycin levels were found in the tissue for both formulations of microspheres throughout the length of the study.

The results of this study suggest that microspheres made of PLGA and tobramycin, with or without PEG, make a suitable biodegradable drug delivery system. These microspheres do not elicit an undesirable inflammatory response, and the formulation can be adjusted to vary the release kinetics of the antibiotic. The microspheres deliver the antibiotic at a near-linear rate for at least four to six weeks. The microspheres remain at the site of implantation but are too small to inhibit tissue regeneration, a characteristic not shared by other suggested antibiotic delivery systems.

Example 2

PLGA/Tobramycin/PMMA

Parenteral Antibiotics

To test the effectiveness in eradicating an established case of osteomyelitis, a study was conducted using a rabbit model of osteomyelitis, wherein the two methods of local antibiotic therapy were tested, i.e., the microspheres and polymethyl methacrylate (PMMA) bone cement against parenteral antibiotics.

Materials and Methods

Forty New Zealand White adult male rabbits, weighing 3-4 kg were selected for this study. Each rabbit underwent an initial surgery to inoculate the radius with bacteria in a well-established procedure. Four weeks later, each rabbit was returned to the operating room for irrigation and debridement surgery and a wound culture. At the time of the second surgery, each animal was randomly placed into one of 5 groups for treatment of the infection:

(1). Control: control group treated with PLGA microspheres containing no antibiotic, (2). Microspheres: PLGA microspheres with 10% tobramycin, (3). Microspheres+Parenteral: PLGA microspheres with 10% tobramycin and parenteral Ancef, (4). Cement+Parenteral: PMMA bead with tobramycin and parenteral Ancef, and (5). Parenteral: parenteral Ancef.

Each animal underwent treatment for four weeks before sacrifice. All animal procedures were approved by our institution's Animal Welfare Committee.

Preparation of the PLGA Microspheres

The double emulsion solvent extraction technique, as described previously, was used to produce microspheres of approximately 15-20 μm diameter containing approximately 10% by weight tobramycin (Nebcin®), from Eli Lilly, Indianapolis, Ind. and 90% by weight 50:50 PLGA (Medisorb®), from Alkermes, Cincinnati, Ohio. These microspheres were blanketed with nitrogen gas, placed in closed vials, and stored frozen at −70° C. until used. Two days prior to surgery the microspheres were sterilized using ethylene oxide gas. For each treated animal, 50 mg of sterilized microspheres was implanted in the debrided bone defect.

Preparation of the PMMA Beads

At the time of irrigation and debridement surgery, PMMA beads were prepared by mixing 20 g of polymethyl methacrylate bone cement (Orthoset®), from Wright Medical, Arlington, Term., with 0.6 g of tobramycin (Nebcin®). The resulting mixture was formed into beads of approximately 4 mm diameter, weighing approximately 0.3 g. One bead was placed into each debrided radius for treatment.

Preparation of the S. aureus Inoculate

The strain of S. aureus used in this study, UAMS-1, was isolated from a patient with osteomyelitis and deposited at the American Type Culture Collection as strain ATCC 49230. The bacteria were prepared from overnight cultures grown in tryptic soy broth at 37° C. with aeration. Cells were harvested by centrifugation, washed with sterile physiological saline, and resuspended to a final concentration of $2 \times 10^8$ CFU/ml (OD of 60% transmittance). Cell suspensions were prepared on the day of surgery and held on ice until implanted.

Minimum inhibitory concentration (MIC) and minimum bactericidal concentration (MBC) for the two antibiotics tested, tobramycin and cefazolin, were determined by standard dilution methods published by the National Committee for Clinical Laboratory Standards. Briefly, S. aureus cells were grown and diluted to 0.5 McFarland turbidity standard, approximately $2 \times 10^8$ cells/ml. The cells were mixed with either of the two antibiotics tested, at concentrations ranging from 2 μg/ml to 64 μg/ml. The following day, the cultures were examined for turbidity to allow determination of MIC values. After this, sample clear cultures were plated to determine the MBC, and colonies counts were done the next day.

Surgical Procedure—Inoculation

All animals were fasted for 24 hours prior to surgery. Anesthesia was induced with ketamine (40 mg/kg) and xylazine (0.5 mg/kg) SQ injection. Anesthesia was maintained using isoflurane titrated to effect. The wound site was prepared with betadine followed by a 70% ethanol rinse, and painted with Prepodyne prior to incision. The incision was made on anterior surface and extended down to the surface of the radius. The periosteum was sharply incised and elevated from the midshaft. A MicroHall™ oscillating saw was used to excise a 1 cm segment from the midshaft of the radius. An inoculum of 10 μl ($2 \times 10^6$ CPU) S. aureus was delivered by microinjection with a sterile pipette tip with an outside diameter of 0.56 mm directly into the center of the medullary canal. The segment was replaced in its original position and the wound closed. All animals were monitored daily for 4 weeks for food and water intake, ambulatory status, and presence of localized and systemic infection (wound swelling, fever, etc.).

Surgical Procedure—Irrigation and Debridement

Four weeks following the date of the initial surgery, the animals were fasted and prepared for the second surgery. Surgical preparation was exactly the same. Once the wound was opened, the infected bone was swabbed and the swab sent for culture. All infected soft tissues and infected bone were removed. The wound was irrigated with 40 cc normal saline through a syringe. If treatment involved a local drug delivery system (groups 1-4), this system was placed before the wound was closed.

Post-operative care included administration of 25 mg/kg cefazolin SC BID (Bums Veterinary Supply, Farmers Branch, Tex.) for animals in groups 3, 4, and 5. For groups 2, 3 and 4, serum and urine were collected three times/day for the first day, once a day for days 2-7, three times/week for week 2, twice/week for weeks 3 and 4. The collected serum and urine samples were assayed for tobramycin concentration. All tobramycin concentrations were performed using fluorescence polarization immunoassay (Abbot TDx System). Sensitivity of the tobramycin assay is defined as the lowest measurable concentration which can be distinguished from zero with 95% confidence and was determined to be 0.18 microgram per milliliter.

Sacrifice and Testing

All animals were sacrificed using an overdose of anesthesia (50-60 mg/kg Pentobarbital administered IV). Weights were obtained. If serum had not been obtained in the week preceding sacrifice, it was obtained at the time of sacrificed and stored frozen until assayed. The radius was removed from each animal and AP and lateral X-rays were obtained. Each x-ray was labeled with tattoo number and the date. The radiographs were evaluated by two blinded observers according to the radiographic grading scale shown in Table 3, below.

TABLE 3

Radiographic Grading Scale

| Categories | Scores |
| --- | --- |
| Size of Defect (length in mm at longest point) | 0-10 |
| New Bone Formation | |
| Full (2 cortices + matrix) | 0 |
| Moderate (2 cortices, no matrix) | 1 |
| Mild (1 cortex) | 2 |
| None | 3 |
| Maximum (worst) Score | 13 |

The forelimb was then stripped of skin and soft tissues and cultures were obtained by swabbing the defect site with a culturette, which was sent for species identification.

Bone samples from the infected radius were divided so that both tobramycin assay and histology analysis could be performed. A 2 cm piece of radius that surrounded the infection site was isolated using a Dremel® saw. This section was divided into proximal and distal halves. One half was randomly chosen and pulverized after freezing in liquid nitrogen (MicroCryoCrusher®, BioSpec Products, Bartlesville, Okla.). The pulverized bone was placed into a glass vial of known weight, weighed and 0.5 cc of PBS was added. This sample was incubated in a 37° C. water bath for 2 hours. The sample was then filtered into a cryogenic container and refrigerated at 4° C. until the assay was performed. The remaining half was placed in a vial containing 10% NBF. Histological samples were decalcified, embedded in paraffin and sections were stained with H&E and Gram stains. These slides were evaluated by a pathologist according to the grading scale given in Table 4, below.

TABLE 4

Histological Grading Scale

| Categories | Scores |
| --- | --- |
| Presence of Bacteria | |
| Marked | 3 |
| Moderate | 2 |

TABLE 4-continued

Histological Grading Scale

| Categories | Scores |
| --- | --- |
| Mild | 1 |
| None | 0 |
| Intraosseous Inflammation | |
| Severe, abscess with fibrosis | 3 |
| Moderate, with fibrosis | 2 |
| Mild, with fibrosis | 1 |
| None, fibrosis only | 0 |
| New Bone Formation | |
| Minimal - <25% | 3 |
| Mild - 25-50% | 2 |
| Moderate - 50-75% | 1 |
| Full - 75-100% | 0 |
| Maximum (worst) Score | 9 |

Results

Tables 5 and 6 show the minimum inhibitory concentration (MIC) and minimum bactericidal concentration (MBC) of tobramycin and cefazolin for this strain of S. aureus bacteria. The numbers are consistent with published values for strains of MRSA.

TABLE 5

MIC and MBC Determinations

| Antibiotic | MIC (µg/ml) | MBC (µg/ml) |
| --- | --- | --- |
| Cefazolin | 2 | 32 |
| Tobramycin | 4-8 | 16 |

TABLE 6

MIC and MBC Determinations

| Concentration of | Turbidity (MIC) | | Colony # (MBC) | |
| --- | --- | --- | --- | --- |
| Antibiotic (µg/ml) | T | C | T | C |
| 0 | ++ | ++ | ND | ND |
| 2 | + | − | ND | ND |
| 4 | + | − | ND | 125 |
| 8 | − | − | 120 | ND |
| 16 | − | − | 0 | 86 |
| 32 | − | − | 0 | 0 |
| 64 | − | − | 0 | 0 |

T = Tobramycin
C = Cefazolin

All rabbits became infected after the inoculum surgery; 100% of the cultures taken at the irrigation and debridement surgery were positive for S. aureus. Most animals developed signs of localized infection such as swelling or drainage at the surgical site but no animals showed signs of systemic disease. All animals were monitored daily for signs of discomfort and were treated to reduce discomfort. Supplemental food was given to animals with diminished appetite and rubber mats were placed in cages to make ambulation more comfortable. After treatment with parenteral cefazolin, some animals had to be treated with metronidazole (Flagyl®, Bums Veterinary Supply) for diarrhea. Three animals died prematurely due to diarrhea.

Figure 4:
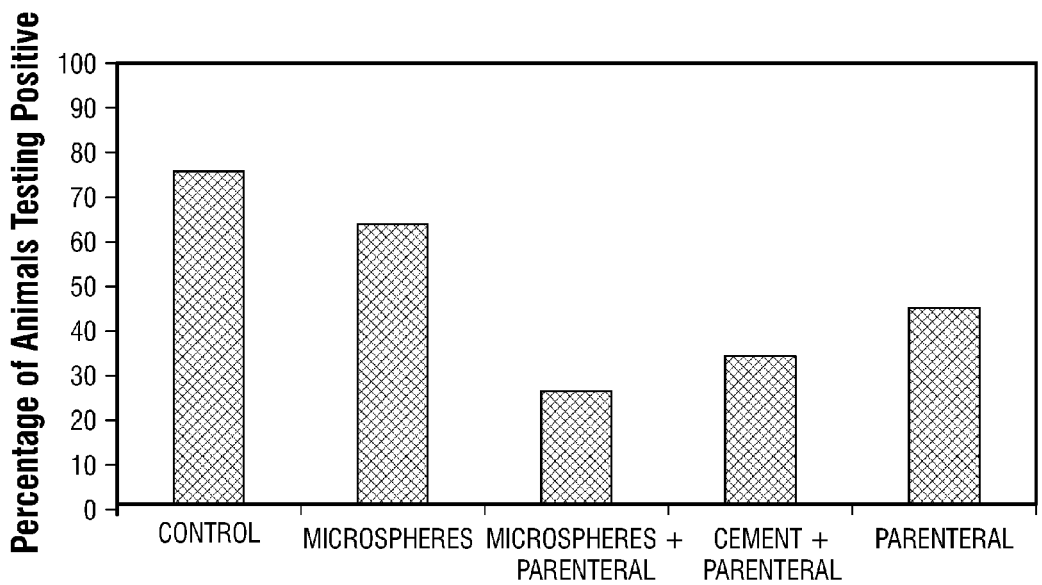
FIG. 4 is a graph illustrating the percentage of animals testing positive for osteomyelitis in a study of rabbits in groups treated with various antibiotic microsphere formulations.

At sacrifice, the percentage of animals testing positive for osteomyelitis ranged from a maximum of 75% in the Control group (1) to a minimum of 25% in the Microspheres+ Parenteral group (3) shown in FIG. 4. Chi-square contingency table analysis shows that only the Microspheres+Parenteral group (3) had a significantly lower percentage than the Control group (1) (p=0.046). However, if all of the groups where parenteral antibiotics were given are grouped together, and the Control and Microspheres groups (1) and (2) are grouped together, these are significantly different (p=0.33).

Figure 5:
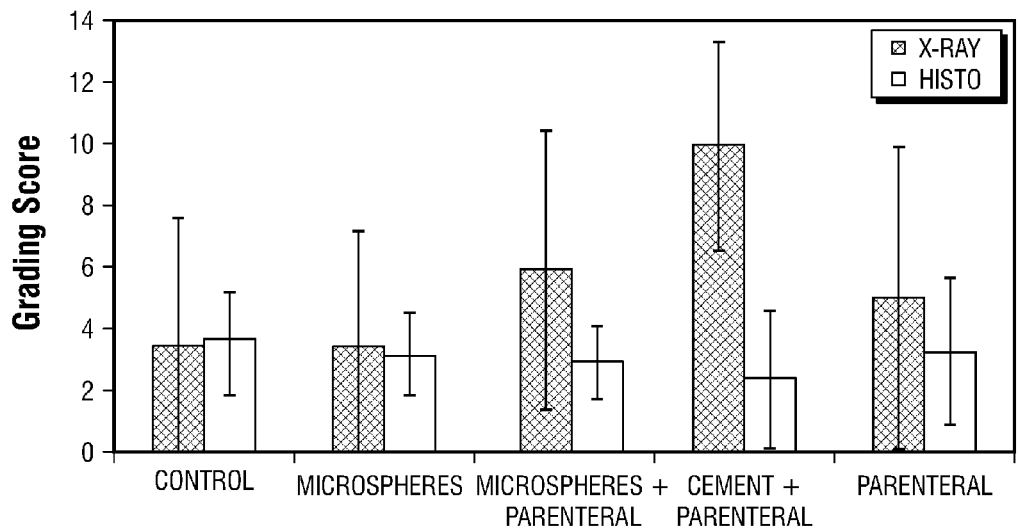
FIG. 5 is a graph illustrating the results of radiographic and histological grading of the bone specimens taken from the rabbit study.

FIG. 5 shows the results of the radiographic and histological grading of the specimens. In the radiographic grading scale, the Cement+Parenteral group (4) score significantly worse than the Control (1), Microspheres (2), and Parenteral (5) groups (p=0.047). In the histological grading, none of the groups were significantly different.

Figure 6:
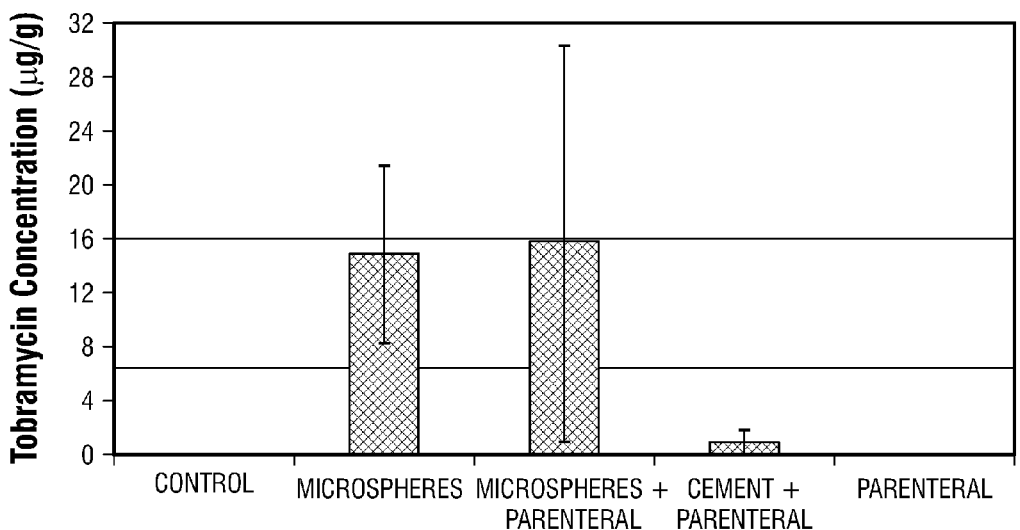
FIG. 6 is a graph illustrating the concentration of tobramycin in the bones for the groups treated locally with tobramycin.

FIG. 6 shows the concentration of tobramycin in the bones for the groups treated locally with tobramycin. At four weeks after implantation of the local carrier system, the microspheres were still releasing significant amounts of tobramycin. The cement samples had small but measurable amounts of tobramycin. All but two of the microsphere samples had concentrations of tobramycin above the MIC and near the MBC level for the bacteria tested, whereas none of the PMMA samples reached the MIC level. None of the tested serum and urine specimens had measurable levels of tobramycin.

Tobramycin-loaded microspheres have been developed and are described herein as a biodegradable drug delivery system for the treatment of osteomyelitis. These microspheres are spherical in shape with an average size of 20 µm. The PLGA copolymers are biocompatible, biodegradable, and approved by the FDA for certain human clinical uses. In-vitro and in-vivo testing in muscle demonstrated that these microspheres deliver antibiotics for longer than four weeks and at nearly linear rates.

The effectiveness of these microspheres has been demonstrated in a rabbit model of osteomyelitis. In this study, all of the animals developed osteomyelitis by four weeks post inoculation. After the second surgery for irrigation and debridement of the wound, most of the animals showed signs of improvement. 25% of the animals in the Control group (1) showed no signs of infection at sacrifice. The only treatment group to demonstrate a significant improvement over the Control was the Microspheres+Parenteral group (3), where 75% percent of the animals showed no signs of infection at sacrifice. No treatment resulted in a 100% success rate.

Thus, the microspheres in accordance with the present invention resulted in high concentrations of tobramycin in the bone four weeks after implantation. The cement beads, by contrast, were still eluting tobramycin but at levels far below the MIC and MBC for the organism studied. In addition, the cement beads created a physical barrier against new bone formation in the debrided infection site. It was this phenomenon that resulted in the Cement+Parenteral group (4) having high (poorer) scores on the radiographic evaluation. Although the high bone tissue levels of tobramycin indicated that the microspheres remained at the site of implantation, the microspheres were small enough to allow new bone formation and degradation of the carrier (PLGA) occurred.

The histological scores indicated that there were no significant differences among any of the five groups studied. Thus, neither the microspheres nor the cement beads resulted in a chronic inflammatory response in the local tissues.

It is also demonstrated herein that these PLGA microspheres deliver antibiotic to the bone tissue at concentrations above or near the MBC for at least four weeks. At four weeks after the onset of treatment, the Microspheres+parenteral group (3) was the only group to demonstrate a significant improvement over the Control group (1). The microspheres in accordance with the present invention do not impede the formation of new bone growth into the debrided site, and do not require a second surgery for removal. The microspheres are biodegradable and do not result in chronic inflammation.

Example 3

PLGA/Vancomycin/PMMA Microspheres

Studies were also performed that are similar to the examples and formulations described above, with vancomycin substituted for tobramycin. In these experiments, microspheres of about 6.86 µm (microns) in diameter containing approximately 5% by weight vancomycin, and microspheres of about 7.46 µm (microns) in diameter containing approximately 10% by weight vancomycin, and 90% by weight 50:50 PLGA were produced. The percentage of PEG in the formulations was either 0% or 5%.

Figure 7:
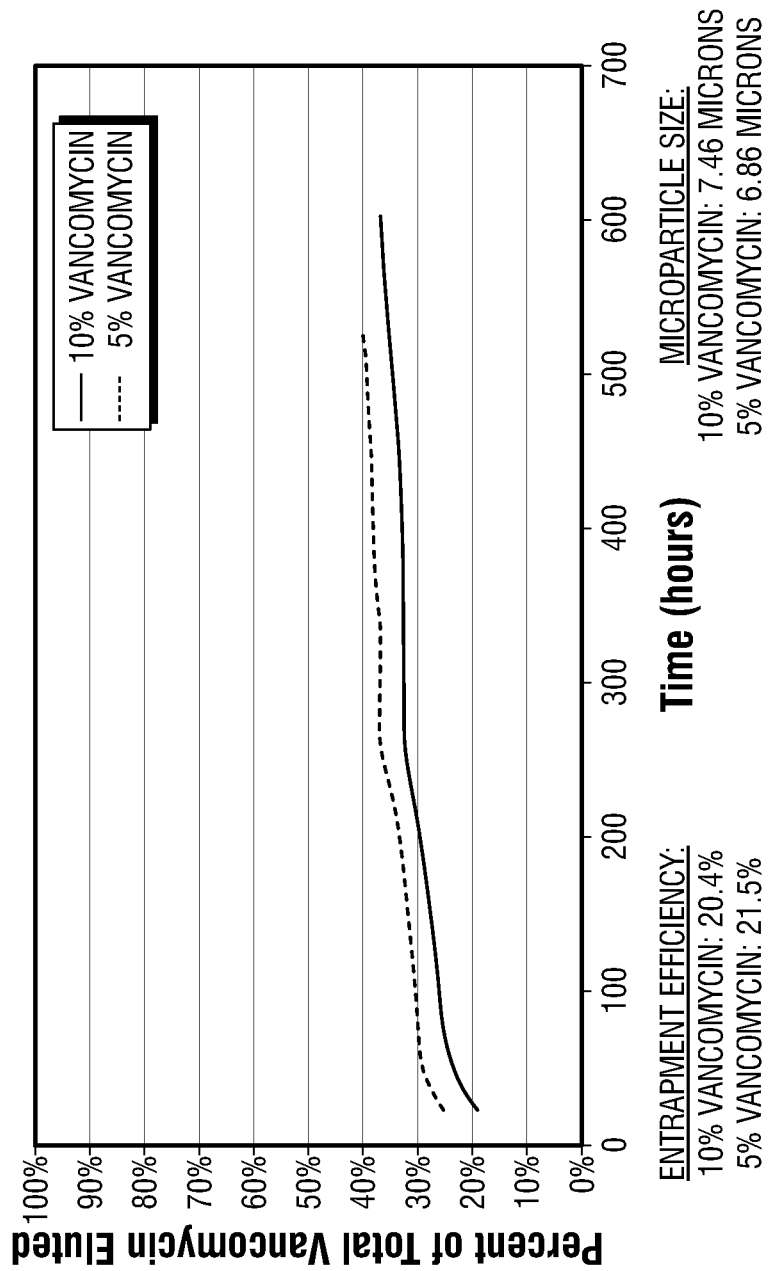
FIG. 7 is a graph illustrating the entrapment efficiency and elution rate over time of various microsphere formulations utilizing vancomycin.

The results of the entrapment efficiencies and elution rates of vancomycin over a period of 600 hours are presented in FIG. 7. The result was that over a 600 hour period, in the 10% vancomycin formulation approximately 27% of the vancomycin was eluted, and in the 5% vancomycin formulation approximately 40% of the vancomycin was eluted. The entrapment efficiency of the 10% vancomycin formulation was found to be approximately 20.4% for the 10% vancomycin formulation and an entrapment efficiency of 21.5% for the 5% vancomycin formulation.

The vancomycin formulation, like the tobramycin formulation is eluted in a very good steady state manner. In both formulations, the levels were acceptable, with only slight differences in entrapment and release. Each of these formulations has advantages, for instance, one may be used as prophylaxis, while the other used for treatment of infection.

Example 4

In the foregoing examples it is demonstrated that antibiotic microspheres about 20±1.6 µm in diameter can deliver a sustained release of antibiotics and can be used to effectively treat an established case of osteomyelitis. Further studies were conducted to test the hypothesis that antibiotic microspheres can be used to prevent infection in a contaminated bony defect in the presence of a metal implant. A rabbit model of osteomyelitis was modified to allow implantation of contaminated porous implants. In half of the surgeries, Trabecular Metal™ cylinders, manufactured by Zimmer, containing antibiotic microspheres were implanted. In the other half of the surgeries, metal cylinders without microspheres were implanted. All implants were inoculated with *Staphylococcus aureus* and the animals were observed for two weeks. Outcome variables that were assessed included both culture results and measurements of bony ingrowth into the porous implants.

Experimental Methods

Fourteen New Zealand White adult male rabbits, weighing 3 to 4 kg each, were selected for this study. Each rabbit underwent bilateral forearm surgeries to remove a 1 cm section of the radius, place a Trabecular Metal™ implant, and inoculate the implant with *Staphylococcus aureus*. In each animal, uncoated implants were placed in the right arm (the control side) while implants coated with antibiotic microspheres were placed in the left arms. The implants used were 5 mm in diameter and 10 mm in length and were shipped sterile from the manufacturer (Zimmer). Each animal was sacrificed 2 weeks later, or when clinical signs of localized infection became apparent. All animal procedures were done in accordance with applicable rules and guidelines.

The method for preparing the microspheres was essentially as described in the foregoing examples. Briefly, a double emulsion-solvent extraction technique was used to produce microspheres of approximately 20 µm diameter containing approximately 5.86% by weight tobramycin (Nebcin®, Eli Lilly, Indianapolis, Ind.) and 94.15% by weight 50:50 PLGA (Medisorb®, Alkermes, Cincinnati, Ohio). These microspheres were blanketed with nitrogen gas, placed in closed vials, and stored frozen at −70° C. until used. For each treated animal, approximately 16 mg of microspheres were implanted in the porous metal cylinder which resulted in a total tobramycin dose of 0.94 mg in each animal.

The strain of *Staphylococcus aureus* used in this study was isolated from a patient with osteomyelitis and deposited at the American Type Culture Collection as strain ATCC 49230. The bacteria were prepared from overnight cultures grown in tryptic soy broth at 37° C. with aeration. Cells were harvested by centrifugation, washed with sterile physiologic saline, and resuspended to a final concentration of $2 \times 10^8$ CFU/ml (optical density of 60% transmittance). Cell suspensions were prepared on the day of surgery and held on ice until implanted.

Minimum inhibitory concentration and minimum bactericidal concentration for tobramycin was determined as previously described above, by standard dilution methods published by the National Committee for Clinical Laboratory Standards. The MIC and MBC for tobramycin against this strain was 4-8 µg/mL and 16 µg/mL, respectively.

Anesthesia was induced with ketamine (40 mg/kg) and xylazine (0.5 mg/kg) by subcutaneous injection and maintained using isoflurane titrated to effect. The wound site was clipped to remove fur and prepared with chlorhexidine. The incision was made on the anterior surface and extended down to the surface of the radius. The periosteum was sharply incised and elevated from the midshaft. A MicroHall oscillating saw (Linvatek, Largo, Fla.) was used to excise a 1 cm segment from the midshaft of the radius. A 5 mm (diameter) by 10 mm (length) cylinder of Trabecular Metal™ (with or without microspheres) replaced the excised radial segment. An inoculum of 10 µL ($2 \times 10^6$ CFU) *Staphylococcus aureus* was delivered by microinjection with a sterile pipette tip directly onto the implant and the wound closed. All animals had a Fentanyl patch placed between the shoulder blades (fur clipped prior to placement) for the first 3 days post-surgery to provide continuous analgesia.

All animals were monitored daily for 2 weeks for food and water intake, ambulatory status, and presence of localized or systemic infection (wound swelling, fever, or other symptoms). Once clinical signs of infection in either arm became obvious, or after two weeks had passed, the animals were euthanized using an overdose of anesthesia (1 ml Beuthanasia administered intravenously). Weights were obtained. In most animals, AP and lateral radiographs were obtained using a C-Arm. Each radiograph was labeled with the animal number and the date.

Figure 8:
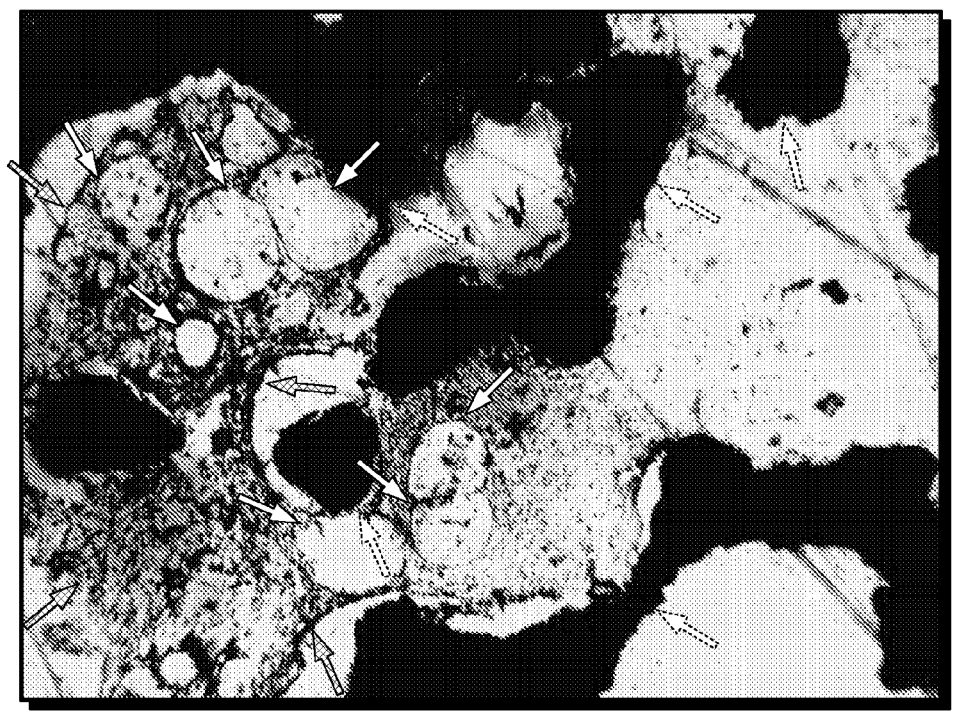
FIG. 8 is a microphotograph of a section taken from a bony defect/metal implant site in a rabbit treated in accordance with the embodiment of the invention. The section was stained with methylene blue and was negative for infection. The antibiotic microspheres appear as clear bubbles (indicated by solid white arrows) and take up 10.12% of the image, the tantalum implant appears as black (indicated by dashed white arrows) and takes up 30.11% of the image, the bone is blue (indicated by crosshatched white arrows) and takes up 17.568% of the image. Thus in this section, the bone is occupying 29.4% of the available space.

Under sterile conditions, the radius was stripped of skin and soft tissues; cultures were obtained by removing tissue adjacent to the implant and sending these specimens for species identification. A 1.5 cm piece of radius that surrounded the implant was isolated and placed in a vial containing 10% neutral buffered formalin for 24 hours and then transferred to 70% ethanol. The samples were imaged using a Faxitron™ to obtain contact radiographs. Histologic samples were prepared by dehydrating with ethanol, infiltrating with Technovit™ plastic and polymerizing the specimen under ultraviolet light. Three sections were prepared from each implant using an Exakt™ system and then stained with methylene blue. An example is shown in FIG. 8. The sections were analyzed using ImageJ™ software to determine the percentage of the implant cross-sectional area that was implant, new bone growth, or empty. These determinations were based solely on color segmentation of the image. In all cases it was verified that these three percentages added up to nearly 100%. If the sum was less than 90% or greater than 110%, the image was reanalyzed by a second observer. The bone area fraction was then calculated as:

$$\frac{(\text{bone \%})}{(100 - \text{implant \%})}$$

Figure 9:
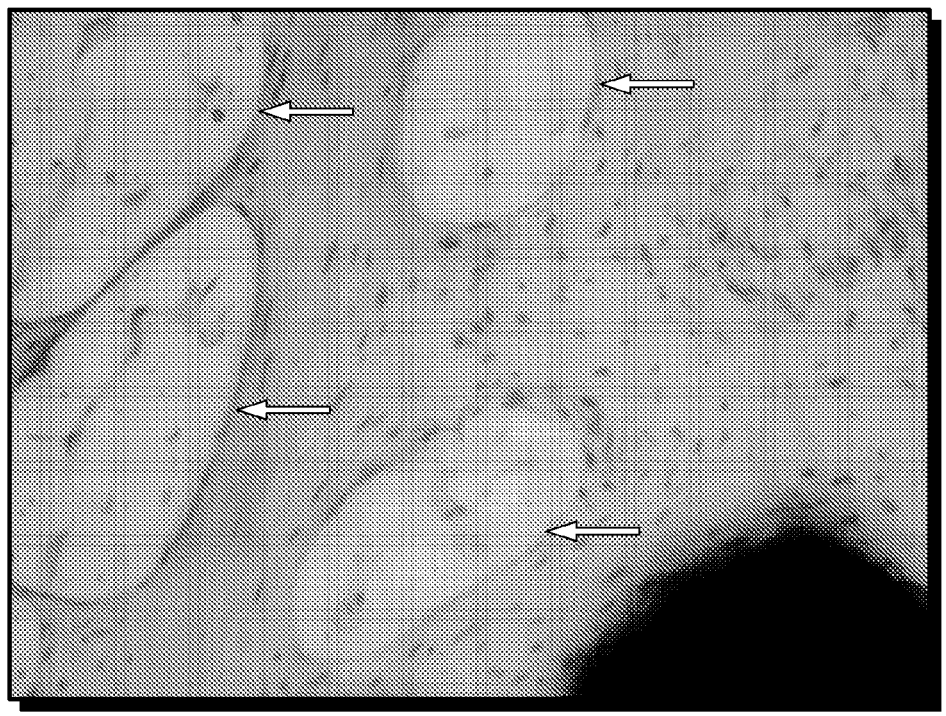
FIG. 9 is a higher magnification microphotograph of another section taken from a bony defect/metal implant site of a rabbit treated in accordance with an embodiment of the invention. This section was stained with methylene blue and basic fuchsin (similar to an H&E stain), and was negative for bacterial growth. The bony ingrowth and the presence of microspheres (clear bubbles indicated by white arrows) inside the tantalum implant (black), are shown. In this image, bone is occupying 100% of the available space, the implant takes up 7.771% of this image, and the microspheres take up 32.924% of this image.

Statistical analysis was performed using SPSS™ version 15 (SPSS Inc, Chicago, Ill.). The proportion of each group testing positive for bacteria at sacrifice was compared using a chi square analysis. For this analysis, the proportion of the untreated side was taken as the expected frequency. Further comparisons to investigate the effect of infection and microspheres in bony ingrowth were performed using T-tests. FIG. 9 is a higher magnification microphotograph of a section taken from a bony defect/metal implant site of a rabbit treated as described above. This section was stained with methylene blue and basic fuchsin (similar to an H&E stain), and was negative for bacterial growth. Within the area of bony ingrowth four microspheres can be seen (indicated by white arrows) inside the tantalum implant (black).

Results

Surgeries were performed on a total of fourteen animals, in three groups of two, six and six. Of these 14 animals, 3 fractured one or both forearms within three days of surgery and were removed from the study. Of the 11 animals that did not sustain a fracture, 2 were sacrificed at 10 days, 1 at 12 days, and 8 were sacrificed after the two week incubation period.

As the 3 animals with the forearm fractures were sacrificed early and were removed from the study, 11 animals remained for analysis. At sacrifice, there were no positive cultures in the left arms (treated with microspheres). In the right arms (untreated controls), there were 7 cultures positive for *Staphylococcus aureus* and 4 cultures were negative. Chi-square analysis demonstrated that the microsphere-treated arms were significantly improved compared to the untreated control arms ($p<0.001$).

The results of the bony ingrowth analysis are presented in Table 7. In all microscopic sections studied, the percent of the cross-sectional area occupied by the implant was approximately 30% (average value 30.39%). Any tissue staining blue was presumed to be bony ingrowth.

TABLE 7

Bone Area Fraction

| Limb | % Bony Ingrowth: Mean (std deviation) |
|---|---|
| Implants with Micro spheres (n = 11) | |
| Contralateral Limb Infected (n = 7) | 28.90 (8.732) |
| Contralateral Limb Not Infected (n = 4) | 46.18 (7.946) |
| Implants without Microspheres (n = 11) | |
| Limb Infected (n = 7) | 19.46 (14.486) |
| Limb Not Infected (n = 4) | 49.01 (9.777) |

The lowest ingrowth numbers were in the limbs that became infected. Using an independent samples t-test to compare bone area fractions from the uninfected limbs (either side) to the infected limbs, the difference was significant (p=0.004). In order to isolate the effect of the microspheres on bony ingrowth, the data from the 4 animals where neither side became infected was analyzed. In these 4 animals the bone area fraction values were not significantly different (p=0.54) when the left side was compared to the right.

The culture results demonstrated that the microspheres were effective in preventing infection in a contaminated wound in the presence of an implant. None of the implants protected with the antibiotic microspheres were culture positive. Notably, not all of the implants on the control side became infected (4 were culture negative). Variations from day to day might be due to variations in the bacteria strain itself since on each day of surgery the bacteria were grown from a separate colony. All 4 of the animals with uninfected control limbs were operated on in the same day and on that day the strain of bacteria might have been less virulent. The bony ingrowth data supports this conclusion. If the bone area fractions from the implants containing microspheres were grouped according to whether the contralateral implant was culture positive or negative, the values are significantly higher for the animals where the contralateral limb did not become infected versus the animals where the contralateral limb did become infected (p=0.01). This may indicate that the bacteria may have been different across the surgery dates, and that the virulence of the bacteria may have had a detrimental effect on the bony ingrowth.

The bony ingrowth data clearly indicated that infection had a detrimental effect on bony ingrowth. This was also apparent on the radiographs (not shown), which demonstrated a loose implant on the infected side.

Even if the microspheres are successful in preventing infection in and around a metal implant in a body defect, it is also important to demonstrate that they do not have detrimental effects on bone and the healing process. It is unlikely that the fractures that 3 animals sustained during the post-operative period were related to the presence of microspheres since both right and left limbs sustained fractures. Further, since the bony ingrowth was not significantly different in the left and right arms of the 4 animals where neither side became infected, the microspheres did not adversely affect bony ingrowth in these animals. FIG. 8 shows a microphotograph of a section where bone can clearly be seen growing within and around the porous implant and several microspheres.

In this study it was found that the implants occupied 30% of the cross-sectional area, but the implants themselves are 75-80% porous by volume. This discrepancy is likely due to the thickness of the sections that were used for image analysis. Plastic sections were cut and then ground to between 20-40 microns thickness, and the entire volume of the section was projected onto a plane during the image acquisition. Theoretically, as the thickness of the section increases, the percentage of the projected area that will be seen as implant will also increase. This will affect the measurements of bony ingrowth, but the effect should be minimal and randomly distributed across all of the sections. These studies demonstrate that the approximately 20 μm diameter microspheres remain at the site of placement of a metal implant (FIGS. 8 and 9), and also suggest that the time-release antibiotic microspheres of that size do not inhibit bony ingrowth. In FIGS. 8 and 9, bone is clearly growing around microspheres, demonstrating that the microspheres do not inhibit bone regrowth. It is thought that sizes slightly larger or smaller than 20 μm also will not inhibit bone ingrowth or regrowth in spaces within and around a metal implant. Sizes much smaller than 20 μm will be susceptible to being phagocytosed as foreign bodies, and thereby removed from the site of implantation. Accordingly, microspheres smaller than about 10 μm will likely not remain at the site of implantation. Microspheres larger than 50 μm in diameter are likely to significantly interfere with bone ingrowth or regrowth. Microspheres larger than about 100-200 microns are likely to markedly inhibit bone regrowth, and are, therefore, preferably excluded.

Although several exemplary antibiotics are described herein, it should be understood that the microspheres employed in the present methods may instead or additionally utilize any other suitable antibiotics and antibacterial agents or combinations thereof. For some applications, antibiotics in the class of "cephalosporins" are preferred. A number of suitable antibiotics and antibacterial agents may be obtained commercially or may be prepared according to the references cited in PHYSICIANS' DESK REFERENCE and the US FDA's Orange book. For example, various embodiments of the present invention may utilize one or more of the following commercially available antibiotics and antibacterial agents selected from the group consisting of: Ancef, Tobramycin, Cefadroxil, Cefazolin, Cephalexin, Cefaclor, Cefotetan, Cefoxitin, Cefprozil, Cefuroxime, Loracarbef, Cefdinir, Cefixime, Cefoperazone, Cefotaxime, Cefpodoxime, Ceftazidime, Ceftibuten, Ceftozoxime, Ceftriaxone, Cefepime, and Vancomycin.

The present controlled release antibiotic microspheres may be implanted injected, or otherwise placed totally or partially within the body at a site of actual or potential infection and deliver an effective amount of the antibiotic agent sufficient to produce bactericidal levels in the body tissues and deliver a near-linear dosage of the antibiotic for at least 4 weeks at levels exceeding the minimum inhibitory concentration (MIC) for organisms commonly found to be the cause of the infections. The microspheres may be placed at a site of surgical treatment, such as a site of a bone fracture, and at one or more sites of placement of metal rods, plates or metallic fixators and joint replacement devices. It is also projected that these or similar microspheres will be useful for deterring or preventing the occurrence of infection at sites where graft or implant materials are used, such as around breast implants, abdominal drains, and so forth, as well in general, gynecologic, cardiovascular, and neurosurgical procedures. The antibiotic microspheres have a diameter large enough to avoid being phagocytosed and removed from the implant site, and are at the same time small enough in diameter to not physically inhibit bone growth at the bony defect site. Use of the microspheres of this size will facilitate or enhance bone ingrowth or regrowth at the implant site, while deterring or preventing infection at the site. In some embodiments, such microspheres are in the range of about 10-50 μm diameter. In some embodiments, the microspheres are in the range of about 10-25 μm in diameter, and in certain embodiments their diameters are in the range of about 15-20 μm.

REFERENCES

1. Mader J T, Landon G C, Calhoun J. Antimicrobial treatment of osteomyelitis. Clin Orthop Relat Res. October 1993(295):87-95.
2. Penner M, Duncan C, Masri B. The in vitro elution characteristics of anti-biotic-loaded CMW and Palacos-R cements. J Arthroplasty. 1999; 14:209-214.
3. Wang J, Calhoun J, Mader J T, LeFrock J. The role and effectiveness of adjunctive therapy in the management of musculoskeletal infections. In: Calhoun J, Mader J T, eds.

Musculoskeletal Infections. New York: Marcel Dekker; 2003:555-585.
4. Ambrose C G, Gogola G R, Clybum T A, Raymond A K, Peng A S, Mikos A G. Antibiotic microspheres: preliminary testing for potential treatment of osteomyelitis. Clin Orthop Relat Res. October 2003(415):279-285.
5. Ambrose C G, Clybum T A, Louden K, et al. Effective treatment of osteomyelitis with biodegradable microspheres in a rabbit model. Clin Orthop Relat Res. April 2004(421):293-299.
6. Cleek R, Ting K, Eskin S, Mikos A. Microparticles of poly(DL-lactic-co-glycolic acid)/poly(ethylene glycol) blends for controlled drug delivery. J Contr Release. 1997; 48:259-268.
7. Bobyn J, Stackpool G, Hacking S, Tanzer M, Krygier J. Characteristics of bone ingrowth and interface mechanics of a new porous tantalum biomaterial. J Bone Joint Surg. 1999; 81-B(5):907-914.
8. Bobyn J, Toh K, Hacking S, Tanzer M, Krygier J. Tissue Response to Porous Acetabular Cups: A Canine Model. J Arthroplasty. 1999; 14(3):347-354.

Without further elaboration, it is believed that one skilled in the art can, using the description herein, utilize the present invention to its fullest extent. The embodiments described herein are to be construed as exemplary only, and not as constraining the remainder of the disclosure in any way. While the preferred embodiments of the invention have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method for controlled release antibiotic treatment of an infection at a site of an existing or potential infection in the body of a patient, comprising:
   formulating a biodegradable microsphere of 6 microns to 25 microns in diameter wherein said microspheres comprise:
      85% to 99% by weight of polylactic-co-glycolic acid (PLGA);
      0.1 to 5% by weight of polyethylene glycol (PEG); and
      1% to 15% by weight of a first antibiotic;
   placing said biodegradable microspheres at said site; and
   inhibiting growth of the infective organism, and enhancing tissue ingrowth at said site by delivering a near-linear dosage of said antibiotic to said site for at least 4 weeks, wherein said dosage exceeds minimum inhibitory concentrations (MIC) for an infective organism.

2. The method according to claim 1, wherein said step of placing the biodegradable microspheres at said site comprises placing said microspheres at a surgical treatment site comprising a bony defect.

3. The method according to claim 1, wherein said step of placing the biodegradable microspheres at said site comprises placing said microspheres at a bone fracture site.

4. The method according to claim 1, wherein said step of placing the biodegradable microspheres at said site comprises placing said microspheres at a site in the body of the patient comprising at least one implanted metal rod, plate or metallic fixator.

5. The method according to claim 1, wherein said step of placing the biodegradable microspheres at said site comprises placing said microspheres at a site in the body of the patient comprising an implanted joint replacement device.

6. The method according to claim 1, wherein said step of placing the biodegradable microspheres at said site comprises placing said microspheres at an existing or potential site of osteomyelitis in the body of the patient.

7. The method of claim 1, wherein said microspheres are formulated to deliver a near-linear dosage of said antibiotic agent for at least the first week of said 4 week period at levels exceeding the minimum inhibitory concentration (MIC) for organisms commonly found to be the cause of infections at such sites.

8. The method according to claim 1, wherein said antibiotic agent is selected from the group consisting of Ancef, Tobramycin, Cefadroxil, Cefazolin, Cephalexin, Cefaclor, Cefotetan, Cefoxitin, Cefprozil, Cefuroxime, Loracarbef, Cefdinir, Cefixime, Cefoperazone, Cefotaxime, Cefpodoxime, Ceftazidime, Ceftibuten, Ceftozoxime, Ceftriaxone, Cefepime, and Vancomycin.

9. The method according to claim 1, wherein said microspheres are about 20 µm in diameter.

10. The method according to claim 1, wherein said microspheres are from 15 µm to 25 µm in diameter.

11. The method according to claim 1, wherein said controlled release comprises near linear release of the antibiotic agent over a 7-28 day period within said 4-week period, with a greater release during the first 24 hours of elution.

12. The method of claim 1, wherein said placing is totally or partially within the body at a site of existing or potential infection.

13. The method of claim 1, wherein said PLGA polymer comprises 50:50: ratio of lactic acid to glycolic acid.

14. The method of claim 1, wherein said microspheres comprise 1% to 10% of said first antibiotic.

15. A method of enhancing tissue ingrowth at a site of infection or potential infection in a patient, comprising:
   inhibiting an infective organism and enhancing tissue ingrowth by:
   1) formulating a biodegradable microsphere of 6 microns to 25 microns in diameter wherein said microspheres comprise:
      85% to 99% by weight of polylactic-co-glycolic acid (PLGA);
      0.1 to 5% by weight of polyethylene glycol (PEG); and
      1% to 15% by weight of a first antibiotic;
   2) placing a microsphere at said site; and
   3) delivering a near-linear dosage of said antibiotic to said site for at least 4 weeks, wherein said dosage exceeds minimum inhibitory concentrations (MIC) for said organism and wherein said microspheres do not undergo phagocytosis.

16. The method of claim 15, wherein said tissue growth is bone ingrowth.

17. The method of claim 16, wherein said microspheres remain at said site for at least thirty days.

18. The method of claim 1, wherein said microspheres remain at said site for at least thirty days.

19. A microsphere configured to enhance tissue ingrowth at a site of infection or potential infection in a patient, wherein said microsphere comprises:

85% to 99% by weight of polylactic-co-glycolic acid (PLGA);
0.1 to 5% by weight of polyethylene glycol (PEG); and
1% to 15% by weight of a first antibiotic; wherein said microsphere delivers a near-linear dosage of the antibiotic to the site for at least 4 weeks, and wherein the microsphere enhance tissue ingrowth by at least 10% compared to bony ingrowth in the absence of the microspheres.

20. The method according to claim 12, wherein said step of placing biodegradable microspheres totally or partially within the body at a site of existing or potential infection comprises implanting or injecting said microspheres at said site.

21. The method according to claim 15, wherein said site comprises existing or potential osteomyelitis.

\* \* \* \* \*